US00PP09363P

United States Patent [19]

Tristram

[11] Patent Number: Plant 9,363

[45] Date of Patent: Nov. 7, 1995

[54] SPIRAEA PLANT NAMED 'WALBUMA'

[76] Inventor: David R. Tristram, Old Rectory, Binsted, Arundel, West Sussex, BN18 OLL, England

[21] Appl. No.: 382,431

[22] Filed: Feb. 2, 1995

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 5,834 12/1986 Huber ..... Plt./54.1

P.P. 7,537 5/1991 Catt ..... Plt./54.1

*Primary Examiner*—James R. Feyrer

*Attorney, Agent, or Firm*—C. A. Whealy

[57] ABSTRACT

A new and distinct cultivar of *Spiraea japonica* named Walbuma, characterized by its compact and spreading habit; small leaves; intense red young shoot and leaf color; early spring growth and early flowering; mature leaves turning gold in sunlight; phenotypic stability and absence of any shoots or leaves reverting to green; and bright pink flower color.

1 Drawing Sheet

The present invention relates to a new and distinct cultivar of Spiraea plant, botanically known as *Spiraea japonica* and referred to by the cultivar name Walbuma. The new variety it also known in the horticultural trade by the name Magic Carpet.

The new cultivar is the result of a breeding and selection program involving several thousand plants and conducted by the inventor at Walberton Nursery in West Sussex, England, with the intent of developing an improvement of the non-patented *Spiraea japonica* cultivar Goldflame. The cultivar Walbuma was discovered by the inventor in the third generation of a seedling selection process. Specifically, the inventor sowed seeds from self-pollinated plants of the cultivar Goldflame, and the best seedling selections were chosen. These selections were self-pollinated, the resulting seeds were sown, and the best seedling selections were chosen by the inventor. These seedling selections were also self-pollinated, the resulting seeds were swon, and the cultivar Walbuma was discovered by the inventor in the third generation of this seedling selection process.

Asexual reproduction of the new cultivar by softwood cuttings taken by the inventor in West Sussex, England, has shown that the unique features of this new Spiraea are stabilized and are reproduced true to type in successive propagations.

The new cultivar has not been observed under all possible environmental conditions. The phenotype may vary somewhat with variations in environment such as temperature, daylength and light intensity, without, however, any variance in genotype. The following observations, measurements, values, and comparisons describe plants grown in West Sussex, England, under outdoor conditions which closely approximate those generally used in commercial horticulture and garden practice.

The following characteristics have been repeatedly observed and are determined to be basic characteristics of Walbuma, which in combination distinguish this Spiraea from the cultivar Goldflame and distinguish it as a new and distinct cultivar:

1. A compact and spreading plant habit. Plants of Goldflame are generally twice as tall as plants of Walbuma.

2. Small leaf size. Leaves of plants of Walbuma are shorter and narrower than leaves of Goldflame.

3. Phenotypic stability. Leaves of plants of Walbuma maintain their golden color when mature without reversion to a dark green color. Portions or entire leaves or shoots of the cultivar Goldflame will revert to a dark green color, regarldess of light level. This indicates phenotypic instability.

4. Intense red color of the young shoots and leaves. Young shoots and leaves of the cultivar Walbuma are more red than young shoots and leaves of Goldflame.

5. Early growth of new shoots and leaves. In the spring, plants of Walbuma form new shoots and leaves one month earlier than plants of Goldflame.

6. Early flowering. Plants of Walbuma form flowers approximately three weeks earlier than plants of Goldflame.

A detailed comparison of the cultivars Walbuma and Goldflame appears in Chart A at the end of the specification.

The accompanying colored photograph illustrates the overall appearance of the new cultivar, showing the colors as true as it is reasonably possible to obtain in colored reproductions of this type. The photograph comprises a top perspective view of a single potted plant of Walbuma.

The following description of the new cultivar is based on plants produced in West Sussex, England, under outdoor conditions in summer with average day temperatures ranging from 12° to 25° C. and average night temperatures ranging from 8° to 14° C. Color references are made to The Royal Horticultural Society Colour Chart except where general terms of ordinary dictionary significance are used.

Botanical classification: *Spiraea japonica* cultivar Walbuma.

Parentage: Three generations of seeding selection from *Spiraea japonica* cultivar Goldflame.

Propagation:

A. *Type.*—By softwood cuttings.

B. *Time to initiate roots, summer.*—8 to 15 days at temperatures of 18° to 22° C.

C. *Rooting habit.*—Fibrous and branching.

Plant description:

A. *General appearance.*—Deciduous shrub. Low growing (25 to 50 cm) and spreading habit. In the northern hemisphere, young shoots and leaves are red in February; as leaves develop, they become gold in color; under full sunlight, mature leaves are more golden; under partial shade, mature leaves are greenish gold; under dense shade, mature leaves are bright green; bright pink flowers develop in June and plants continue to flower throughout the summer under good growing conditions.

B. *Foliage description.*— 1. Leaf shape: Ovate. 2. Leaf margin: Serrate. 3. Leaf apex: Acute. 4. Leaf base: Obtuse. 5. Leaf aspect: Concave along central vein, becoming flat with maturity. 6. Leaf length: 25 to 60 mm. 7. Leaf width: 15 to 30 mm. 8. Leaf texture: Top and under sides glabrous and dull. Veins prominent on under side. 9. Leaf color: a. Young leaves, beginning to expand: (1) Top side: Red, 182A. (2) Under side: Dark red, 187C. b. Young leaves, halfway expanded: (1) Top side: Red-brown, 176C. (2) Under side: Dark red, 184B. c. Fully expanded leaves in full sunlight: (1) Top side: Gold, 153D. (2) Under side: Light green, 146D. d. Fully expanded leaves in partial shade: (1) Top side: Greenish gold, 151A. (2) Under side: Light green, 147C. e. Fully expanded lower leaves, completed shaded: (1) Top side: Bright green, 143B. (2) Under side: Light green, 139D. 10. Petiole length: 1.5 mm. 11). Petiole color: a. Young leaves, beginning to expand: 182A. b. Young leaves, halfway expanded: 176C. c. Fully expanded leaves, full sunlight: 153D. d. Fully expanded leaves, partial shade: 151A. e. Fully exapnded lower leaves, dense shade: 143B.

Flowering description:

A. *Inflorescence.*—Flowers borne in slightly domed compound terminal corymbs with a 20 to 60 mm diameter.

B. *Natural flowering season.*—Natural flowering season in June and July in the northern hemisphere.

C. *Quantity of flowers.*—Each corymb is comprised of 20 to 200 individual flowers.

D. *Individual flowers.*— 1. Diameter: 6 to 9 mm. 2. Petals: a. Quantity: 5. b. Length: 2 to 3 mm. c. Width: 2 to 3 mm. d. Color: Both top and under sides, bright pink, 67D. 3. Sepals: a. Quantity: 5. b. Color: Both top and under sides, typically dark red, 59A.

E. *Reproductive organs.*— 1. Styles: a. Quantity: 5. b. Length: 1 to 2 mm. c. Color: Reddish pink, 59D. 2. Anthers: a. Quantity: 10. b. Aspect: Prominent, projecting above flowers. c. Color: Dark red, 59A. 3. Filaments: a. Length: 5 to 8 mm. b. Color: Bright pink, 67D.

Disease resistance: No marked susceptibility nor resistance to fungal, bacterial or viral pathogens had been noted.

CHART A

| CHARACTERISTIC | WALBUMA | GOLDFLAME |
|---|---|---|
| PLANT HEIGHT | 25 to 50 cm | 50 to 90 cm |
| LEAF LENGTH | 25 to 60 mm | 40 to 70 mm |
| LEAF WIDTH | 15 to 30 mm | 20 to 60 mm |
| LEAF COLOR: | | |
| YOUNGEST LEAVES, TOP SIDE | 182A | 183B |
| YOUNGEST LEAVES, UNDER SIDE | 187C | 187C |
| HALF-EXPANDED LEAVES, TOP SIDE | 176C | 177C |
| HALF-EXPANDED LEAVES, UNDER SIDE | 184B | 177D |
| FULLY EXPANDED LEAVES, SUN, TOP SIDE | 153D | 153D |
| FULLY EXPANDED LEAVES, SUN, UNDER SIDE | 146D | 146D |
| FULLY EXPANDED LEAVES, SHADE, TOP SIDE | 151A | 151A |
| FULLY EXPANDED LEAVES, SHADE, UNDER SIDE | 147C | 147C |
| SHADED LOWER LEAVES, TOP SIDE | 143B | 144B |
| SHADED LOWER LEAVES, UNDER SIDE | 139D | 139D |
| FLOWER DIAMETER | 6 to 9 mm | 5 to 7 mm |
| PETAL LENGTH | 2 to 3 mm | 1.5 to 3 mm |
| PETAL WIDTH | 2 to 3 mm | 1 to 2 mm |
| PETAL COLOR | 67D | 68B |
| SYTLE LENGTH | 1 to 2 mm | 1 to 1.5 mm |
| STYLE COLOR | 59D | 60C |
| FILAMENT LENGTH | 5 to 8 mm | 2 to 6 mm |
| FILAMENT COLOR | 67D | 59D |

I claim:

1. A new and distinct cultivar of *Spiraea japonica* named Walbuma, as illustrated and described.

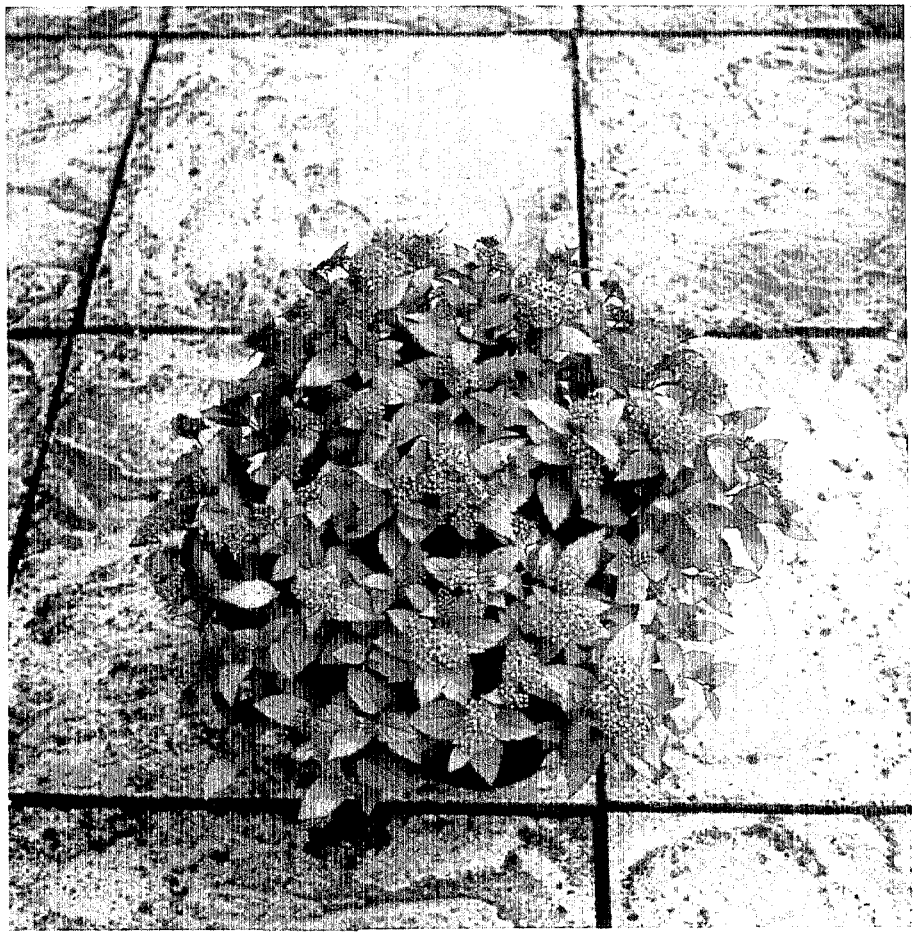

* * * * *